US00PP31228P3

(12) United States Plant Patent
Hansen

(10) Patent No.: US PP31,228 P3
(45) Date of Patent: Dec. 10, 2019

(54) *SEDUM* PLANT NAMED 'POPSTAR'

(50) Latin Name: ***Sedum* hybrid**
Varietal Denomination: Popstar

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 76 days.

(21) Appl. No.: 15/932,141

(22) Filed: Feb. 9, 2018

(65) Prior Publication Data

US 2019/0254216 P1 Aug. 15, 2019

(51) Int. Cl.
*A01H 5/02* (2018.01)
*A01H 6/32* (2018.01)
*A01H 6/00* (2018.01)

(52) U.S. Cl.
USPC ..... Plt./479
CPC ..... *A01H 6/00* (2018.05); *A01H 5/02* (2013.01)

(58) Field of Classification Search
USPC ..... Plt./479, 373
CPC ... A01H 5/02; A01H 5/00; A01H 5/10; A01H 6/328; A01H 6/749; A01H 6/32
See application file for complete search history.

(56) References Cited

U.S. PATENT DOCUMENTS

PP22,094 P2 * 8/2011 Gossett ..... A01H 5/02 Plt./479
PP22,191 P2 * 10/2011 Dozier, Jr. ..... A01H 5/08 Plt./156
PP22,457 P2 * 1/2012 Hansen ..... A01H 5/02 Plt./479
PP26,191 P3 * 12/2015 Egger ..... A01H 5/02 Plt./479

OTHER PUBLICATIONS

Bovio. Issuu Michigan Gardener 2017 Perennial Perspectives *Sedum*, retrieved on Jan. 14, 2019, retrieved from the Internet at https://issuu.com/michigangardener/docs/mg.sep.17, cover page, pp. 28-30. (Year: 2017).*
Germania Seed Company Program #49 2017 Walters Gardens Bare Root and Plug Perennials,retrieved on Jan. 28, 2019, retrieved from the Internet at https://www.germaniaseed.com/pdf/2018/749_walters.pdf, pp. 1, 19 22. (Year: 2017).*

* cited by examiner

*Primary Examiner* — June Hwu

(57) ABSTRACT

The new and distinct cultivar of perennial *Sedum* plant named 'Popstar' is characterized by tight-forming compact clumps with small-sized, blue-green glaucous foliage blushed with greyed-purple on vertical to slightly arching branching stems flower stems that resist falling over and opening up in the center of the plant throughout the growing season. Numerous stems produce a multitude of flowers of mauve-pink effect completely covering the top of the plant. The new plant is useful for the landscape in containers, as specimens, en masse.

2 Drawing Sheets

Botanical designation: *Sedum* hybrid.
Cultivar denomination: 'Popstar'.

BACKGROUND OF THE INVENTION

The present invention relates to a new and distinct cultivar of *Sedum* plant, botanically known as *Sedum* and hereinafter referred to by the cultivar name 'Popstar'. There are over 300 recognized species of the genus *Sedum*.

The new *Sedum* plant is a selection of a planned breeding program conducted by the inventor, at a wholesale perennial nursery in Zeeland, Mich., USA.

The new *Sedum* plant was selected as a single seedling from an insect pollinated cross in an isolation block in late summer of 2012 between a selection of *Sedum cauticola* (not patented) as the female or pod parent and the proprietary unreleased mutation known as "SRF-SED-282-F 'Sunset Cloud'" (not patented) as the male or pollen parent. *Sedum* 'Popstar' was assigned the breeder code number 12-49-5 to keep it separated from among thousands of other seedlings of this and other crosses when it progressed through the initial trial phase in the fall of 2014. The selected single seedling clone was originally selected for it strong, healthy, upright growth, colorful foliage and flowers.

Asexual reproduction of *Sedum* 'Popstar' by vegetative shoot tip cuttings at a wholesale perennial nursery in Zeeland, Mich., USA since the spring of 2015, has shown that the unique features of this new *Sedum* plant are stable and reproduced true to type in successive generations.

No plants of *Sedum* 'Popstar' have been sold or disclosed by this or any other name, in this country or anywhere in the world, exception that which was either derived directly or indirectly from the inventor and disclosed within one year of the filing of this application.

SUMMARY OF THE INVENTION

Plants of *Sedum* 'Popstar' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of

*Sedum* 'Popstar' and distinguish it as a new and distinct autumn stonecrop plant unique from all other autumn stonecrop plants known to the inventor:

1. Tight-forming compact clumps with vertical to arching stems.
2. Center stems remain erect throughout the growing season produce full habit.
3. Small-sized, blue-green, glaucous foliage with blushing of greyed-purple.
4. Numerous, branched, greyed-purple stems produce flower clusters of mauve-pink completely cover the top of the plant.

In comparison with the female parent, the new plant has a larger width and height and retains its upright stems better through the entire growing season. The nearest comparison variety known to the inventor is 'Dazzleberry' U.S. Plant Pat. No. 22,457. The new plant is slightly taller in flowering height size and has lighter colored flowers. Compared with 'Crystal Pink' U.S. Plant Pat. No. 22,094 the new plant is shorter in flower with more flower coverage and develops a deeper pink flower. Compared with 'Marina' U.S. Plant Pat. No. 26,191 the new plant is taller, with more stiffly upright stems, more rounded leaves. 'Superstar' U.S. Plant patent application Ser. No. 15/931,171 has dark turquoise foliage with smoky gray overlay and the flowers are rosy pink with hot pink carpels that mature to dark purple fruit. The male parent foliage is darker greyed-purple, the habit is more arching and open in the center and the flowering is not as profuse.

BRIEF DESCRIPTION OF THE PHOTOGRAPHS

The photograph of the new plant demonstrates the unique traits and the overall appearance of *Sedum* 'Popstar'. The colors are as accurate as reasonably possible with color reproductions of this type. Variations in ambient light spectrum, source and direction may cause the appearance of minor variation in color. The plants used in the photograph were three-year-old plants grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
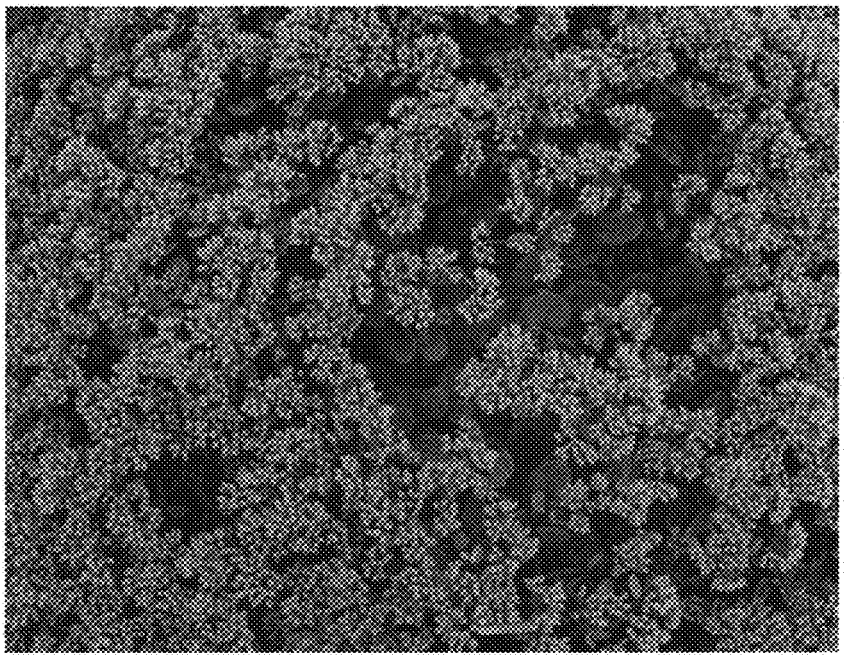
FIG. 1 shows the plant in early stages of flowering with foliage.
Figure 2:
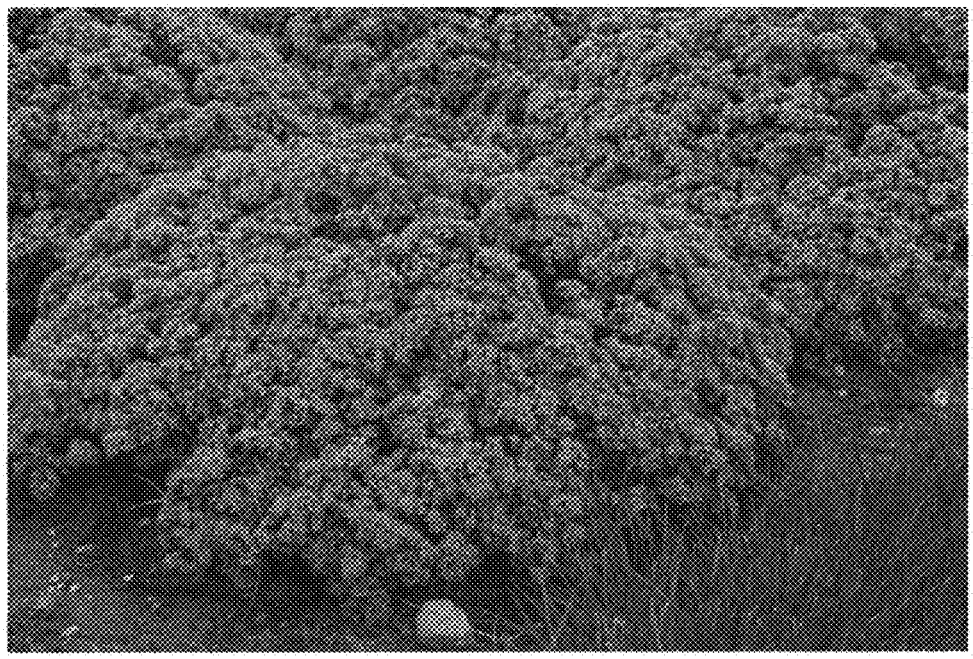
FIG. 2 shows the plant in full flower coverage.
Figure 3:
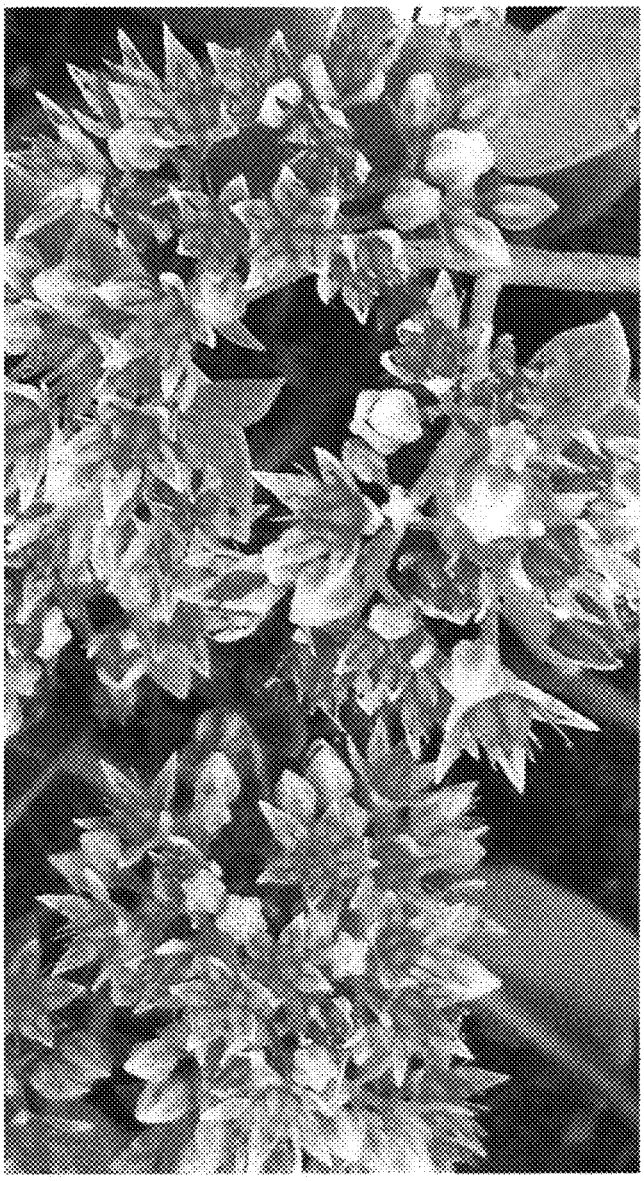
FIG. 3 shows a close-up of the flower and buds.

The following is a detailed description of three-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Popstar';

Parentage: A selection of *Sedum cauticola* plant as the female, or seed, parent; "SRF-SED-282-F 'Sunset Cloud'" (not patented) as the male or pollen parent;

Asexual propagation: Stem tip cuttings and division;

Time to initiate roots: About two weeks;

Time to finish a 3.8 liter flowering container: About three months in the summer from a rooted 2.5 cm plug;

Root description: Thick, fleshy; freely branching; creamy white to light tan in color.

Plant habit: Winter-hardy herbaceous perennial; clumping mound; stems stiff and upright to arching arising from a dense crown; dense and full, not opening in center later in the season; flower heads freely branching;

Growth rate: Moderately vigorous;

Plant size: About 28.5 cm tall and 76.0 cm wide in full flower;

Stems: Terete, glaucous, glabrous; diameter at base average about 2.5 mm and about 22.0 cm long from base to initial branches; internodes average about 1.2 cm; about 380 stems per plant;

Stem color: Nearest RHS 183D;

Lateral branches: Glaucous; primary branches about 2.2 mm diameter and about 6.0 cm long;

Lateral branch color: Nearest RHS 183D;

Foliage: Ovate-orbicular; alternate to sub-opposite; simple; smooth, glabrous, glaucous on both surfaces; distally sessile; thick, fleshy and succulent; apex bluntly acute to rounded; base rounded; margin irregularly and shallowly dentate, primarily in distal one half of leaf, about 2.0 mm to 6.5 mm apart; decreasing in size distally; attitude outward;

Foliage size: To about 3.5 cm long, 3.0 cm across and 2.0 mm thick; average about 3.1 cm long, 2.6 cm across and 1.7 mm thick;

Foliage color: Adaxial nearest RHS N138C, abaxial between RHS N138C and RHS 148B with tinting of nearest RHS 187B on the toothed margin;

Petiole: In proximal leaves, becoming sessile distally; concavo-convex; to about 4.0 mm long and 2.8 mm across; average about 2.0 mm long and 2.5 mm across;

Petiole color: Adaxial and abaxial nearest RHS N148C, with maculate speckles on adaxial surface nearest RHS 185B;

Venation: Palmate, barely distinguishable; slightly raised abaxial;

Vein color: Abaxial and adaxial veins same as surrounding leaf tissue; abaxial midrib maculate with blend of RHS 185B and RHS 187B, adaxial midrib lightly maculate in proximal 5.0 mm with blend of RHS 185B and RHS 187B;

Flower: Stellate, actinomophic; pentamerous; persistent; attitude upright to outwardly in terminal compound cymes; about 7.0 mm across and 4.0 mm deep;

Flower number: About 5,000 to 8,000 flowers per plant;

Fragrance: None detected;

Flowering season: Beginning late August to late September in Zeeland, Mich.; able to be forced to flower in greenhouse out of season with about 2 months of growth following 9 weeks of vernalization;

Longevity: Flower cymes remain effective for about three weeks on the plant and one week as cut flowers; individual flowers persistent and effective for about three weeks;

Flower buds about one day prior to opening: Broadly ellipsoidal with five angular sides, semi-carinate; apex broadly acute; base rounded; about 3.2 mm diameter and about 4.2 mm long; shallowly longitudinally sulcate;

Flower bud color: Longitudinally striped alternately with nearest RHS N155B and a blend between RHS 75C and RHS 76B; color of buds about ten days prior to opening nearest blend between RHS 90D and RHS N187C;

Inflorescence: About 7.0 cm tall from first branch and about 7.5 cm across; up to about 65 flowers per inflorescence;

Petals: Typically five, broadly-lanceolate; acute apex, base fused, margin entire; glabrous abaxial and adaxial; average about 4.0 mm long and about 2.0 mm across at fusion;

Petal color: Adaxial nearest RHS 76C; abaxial along longitudinal margins between RHS 76C and RHS 77D with midrib lighter than RHS 76D;

Calyx: With five sepals, fused at base; adpressed to petals, about 1.5 mm long and about 2.5 mm diameter;

Sepals: Campanulate; lanceolate; acute apex; fused base; margin entire; glabrous and slightly glaucous both abaxial and adaxial; about 1.2 mm long and about 1.0 mm wide at fused base;

Sepal color: Abaxial and adaxial nearest RHS 90D and RHS N187D;

Peduncles: Terete; slightly glaucous, glabrous; stiff and flexible; freely branching; upright to slightly outwardly; with branches to about 50 degrees from perpendicular; about 7.0 cm long and 2.5 mm diameter;

Peduncle color: Blend between RHS 90D and RHS N187C;

Pedicels: Terete; glabrous, slightly glaucous; strong and stiff, yet flexible; about 3.5 mm long and 0.7 mm diameter;

Pedicel color: Blend between RHS N138D and RHS 186C;

Androecium: Typically ten stamens;

*Filaments*.—Outwardly; about 3.8 mm long and about 0.2 mm diameter; color nearest RHS N79C.

*Anthers*.—Basifixed, longitudinal; globose to ellipsoid; about 0.7 mm long and 0.6 mm diameter; color nearest RHS N79B.

*Pollen*.—Moderate in quantity; color nearest RHS 18B.

Gynoecium: Typically five; cylindrical, conic in distal one third; about 4.0 mm long and 1.2 mm diameter;

*Style*.—Terete; about 0.5 mm long and 0.5 mm diameter at point of attachment to ovary; glabrous; color nearest RHS N155B.

*Stigma*.—Minute, globose; about 0.2 mm diameter and 0.2 mm long; color nearest RHS N155B.

*Ovary*.—Nearly terete, acutely tapering at apex to style; base truncate; lustrous; about 3.5 mm long and 1.2 mm diameter; color lighter than RHS N66D when first opening and nearest RHS 67A when pollen dehisced.

Fruit: Ventrally dehiscent follicle; about 3.5 mm long and 3.2 mm across; color at maturity nearest RHS 177A;

Seed: Sparse; fine; lanceolate; about 1.0 mm long and less than 0.2 mm across; color between RHS 165A and RHS 165B;

Disease and pest resistance: Plants of the new *Sedum* 'Popstar' is xeromorphic and grow best with good drainage, full sun and moderate to low fertility. 'Popstar' is cold hardy from USDA zones 3 to 9 and has tolerated temperatures of at least 35 degrees C. 'Popstar' tolerates heavy rains and wind and is not prone to develop an open center later in the season as many other *Sedum* cultivars do. Other pest and disease resistance and tolerance outside that normal for *Sedum* is not known.

It is claimed:

1. The new and distinct perennial *Sedum* plant named 'Popstar' as herein described and illustrated.

* * * * *